(12) United States Patent
Tozuka et al.

(10) Patent No.: US 10,145,814 B2
(45) Date of Patent: Dec. 4, 2018

(54) INTERNAL SOLUTION FOR REFERENCE ELECTRODE, REFERENCE ELECTRODE, AND GLASS ELECTRODE

(71) Applicants: KABUSHIKI KAISHA PILOT CORPORATION, Tokyo (JP); HORIBA Advanced Techno, Co., Ltd., Kyoto-shi, Kyoto (JP)

(72) Inventors: Taro Tozuka, Hiratsuka (JP); Yuji Nishio, Kyoto (JP); Akio IShii, Kyoto (JP)

(73) Assignees: KABUSHIKI KAISHA PILOT CORPORATION, Tokyo (JP); HORIBA ADVANCED TECHNO, CO., LTD., Kyoto-Shi, Kyoto (JP)

(*) Notice: Subject to any disclaimer, the term of this patent is extended or adjusted under 35 U.S.C. 154(b) by 91 days.

(21) Appl. No.: 15/115,610

(22) PCT Filed: Jan. 30, 2015

(86) PCT No.: PCT/JP2015/052633
§ 371 (c)(1),
(2) Date: Jul. 29, 2016

(87) PCT Pub. No.: WO2015/115587
PCT Pub. Date: Aug. 6, 2015

(65) Prior Publication Data
US 2017/0168003 A1     Jun. 15, 2017

(30) Foreign Application Priority Data
Jan. 31, 2014   (JP) .................................. 2014-016958

(51) Int. Cl.
*G01N 27/30* (2006.01)
*G01N 27/36* (2006.01)

(52) U.S. Cl.
CPC ......... *G01N 27/301* (2013.01); *G01N 27/302* (2013.01); *G01N 27/36* (2013.01)

(58) Field of Classification Search
None
See application file for complete search history.

(56) References Cited

U.S. PATENT DOCUMENTS

| 5,254,634 A | 10/1993 | Ito et al. |
| 2005/0202313 A1 | 9/2005 | Franzheld et al. |

(Continued)

FOREIGN PATENT DOCUMENTS

| CN | 101512332 A | 8/2009 |
| CN | 102680522 A | 9/2012 |

(Continued)

OTHER PUBLICATIONS

European Patent Office, Extended European Search Report Issued in European Application No. 15743191.7, dated Sep. 11, 2017, Germany, 14 pages.

(Continued)

*Primary Examiner* — Eli S Mekhlin
(74) *Attorney, Agent, or Firm* — Alleman Hall Creasman & Tuttle LLP

(57) ABSTRACT

In order to improve the endurance of this internal solution for a reference electrode beyond that in the prior art, the solution is made to contain a copolymerized material of a crosslinker having a plurality of non-acrylamide functional groups, and a non-acrylamide monofunctional hydrophilic monomer.

3 Claims, 4 Drawing Sheets

(56) References Cited

U.S. PATENT DOCUMENTS

| | | | |
|---|---|---|---|
| 2007/0020527 A1 | 1/2007 | Ehrismann et al. | |
| 2010/0179046 A1* | 7/2010 | Iwamoto | C03C 3/095 501/41 |
| 2012/0226459 A1* | 9/2012 | Komatsu | G01N 27/4163 702/85 |

FOREIGN PATENT DOCUMENTS

| | | |
|---|---|---|
| DE | 3228647 A1 | 2/1984 |
| DE | 102011089707 A | 9/2012 |
| DE | 102012102321 A1 | 9/2013 |
| EP | 0495107 A1 | 7/1992 |
| JP | 2001255298 A | 9/2001 |
| JP | 2004004011 A | 1/2004 |
| JP | 2007524090 A | 8/2007 |
| JP | 2009288117 A | 12/2009 |
| WO | 9201721 A1 | 2/1992 |
| WO | 2013139758 A1 | 9/2013 |

OTHER PUBLICATIONS

ISA Japan Patent Office, International Search Report Issued in Application No. PCT/JP2015/052633, dated Apr. 28, 2015, WIPO, 4 pages.

* cited by examiner

INTERNAL SOLUTION FOR REFERENCE ELECTRODE, REFERENCE ELECTRODE, AND GLASS ELECTRODE

TECHNICAL FIELD

The present invention relates to an internal solution for a reference electrode, a reference electrode that uses this internal solution, and a glass electrode that is used together with this reference electrode.

BACKGROUND ART

An electrode such as that described, for example, in Patent document 1 is known as an electrode used in a pH meter. In particular, an electrode that uses a gel-like composition such as that described in Patent document 2 as an internal solution is widely known as a reference electrode that is used in this pH meter.

This gel-like composition can be manufactured by means of a comparatively simple process in which a monomer is made to undergo a polymerization reaction in a solvent, and it is anticipated that, starting with the internal solution of an electrode, this gel-like composition will be applicable to a wide range of uses.

Note that the gel-like composition referred to here is a dispersion type of gel, and describes a substance in a semi-solid state that has lost its fluidity while maintaining a high level of viscosity by means of its dispersoid network, and includes solid sols, which, broadly speaking, are solid dispersion medium colloids.

However, the above-described gel-like compositions have the problem that they have inferior durability. In addition to this, in reference electrodes that use this gel-like composition as their internal solution, a sizeable liquid junction potential is generated in the case of an alkaline test sample, and this leads to a corresponding increase in measurement errors.

SUMMARY OF THE INVENTION

Technical Problem

Patent document 1: Japanese Patent Application Laid-Open (JP-A) No. 2009-288117
Patent document 2: Japanese Patent Application Laid-Open (JP-A) No. 2007-524090

Solution to the Problem

The present invention was conceived in in order to solve the above-described problems, and it is an object thereof to improve the durability of the internal solution of a reference electrode beyond what is obtainable from the conventional technology.

Namely, a reference electrode internal solution according to the present invention contains a copolymerization of a cross-linking agent having a plurality of functional groups excluding acrylamide, and a monofunctional hydrophilic monomer excluding acrylamide.

According to this reference electrode internal solution, because the reference electrode internal solution contains a copolymerization of a cross-linking agent having a plurality of functional groups and a monofunctional hydrophilic monomer, a cross-linking structure is formed in this copolymerized substance, and the durability of the reference electrode internal solution can be improved beyond what is obtainable from the conventional technology.

Moreover, when a strongly toxic substance is to be used as the substance that is to undergo the copolymerization reaction, then by excluding highly toxic acrylamides, the level of risk can be greatly reduced in hazardous situations such as the manufacturing process, or when handling the manufactured internal solution and the reference electrode that uses this internal solution.

In order to make it possible to reduce the liquid junction potential even when the test sample is an alkaline sample, and to accurately measure the test samples over a broad pH range, it is preferable for the cross-linking agent to be an acrylate or methacrylate, and it is also preferable for the hydrophilic monomer to be an acrylate or methacrylate.

In order for the reference electrode internal solution to have excellent pressure resistance and heat resistance, and to reduce deterioration caused, for example, by steam sterilization and thereby improve the repetition durability thereof, the cross-linking agent is a monomer having a plurality of functional groups, and examples thereof include acrylates having a plurality of functional groups, methacrylates having a plurality of functional groups, amines having a plurality of functional groups, and vinyl compounds having a plurality of functional groups, and the like. Preferable examples of an acrylate or methacrylate include glycerine diacrylate, polyalkylene glycol diacrylate, polyalkylene glycol triacrylate, ethoxylated bisphenol A diacrylate, ethoxylated glycerine triacrylate, trimethylolpropane triacrylate, trimethylolpropane trimethacrylate, polyalkylene glycol dimethacrylate, glycerine dimethacrylate, polyalkylene glycol trimethacrylate, and the like. Examples of an amine having a plurality of functional groups include triethylenetetramine, ethylenediamine, hexamethylenediamine, dipropylenetriamine, and the like. Examples of a vinyl compound having a plurality of functional groups include divinylbenzene, butanediol divinyl ether, diethylene glycol divinyl ether, and the like.

Examples of a hydrophilic monomer include alkylaminoalkyl acrylates, and polyhydric alcohol acrylates, as well as alkoxy ether derivatives thereof, acryloyloxy ethyl succinic acid, acryloyloxy ethyl acid phosphates, 2-(acryloyloxy) ethane sulfonic acid, 3-sulfopropyl potassium acrylates, alkyl amino alkyl methacrylates, and polyhydric alcohol methacrylates, as well as alkoxy ether derivatives thereof, methacryloyloxy ethyl succinic acid, methacryloyloxy ethyl acid phosphates, 2-(methacryloyloxy) ethane sulfonic acid, 3-sulfopropyl potassium methacrylates, and the like.

Examples of the aforementioned alkyl amino alkyl methacrylates include dimethylaminoethyl methacrylates as well as quaternary compounds thereof, diethylaminoethyl methacrylates as well as quaternary compounds thereof, dipropylaminoethyl methacrylates as well as quaternary compounds thereof, N, N, N-trimethyl-(2-hydroxy-3-methacryloyloxy) propyl ammonium chloride, and the like.

Examples of the aforementioned alkyl amino alkyl acrylates include dimethylaminoethyl acrylates as well as quaternary compounds thereof, diethylaminoethyl acrylates as well as quaternary compounds thereof, dipropylaminoethyl acrylates as well as quaternary compounds thereof, N, N, N-trimethyl-(2-hydroxy-3-acryloyloxy) propyl ammonium chloride, and the like.

Examples of a polyhydric alcohol methacrylate and alkoxy ether derivatives thereof include glycerine methacrylate, and ethylene glycol methacrylate monomers, while specific examples of an ethylene glycol methacrylate monomer include methacrylate monomers such as polyethylene glycol monomethacrylate, methoxypolyethylene glycol monomethacrylate, and polyethylene glycol monomethacrylate and the like.

Examples of a polyhydric alcohol acrylate and alkoxy ether derivatives thereof include glycerine acrylate, and ethylene glycol acrylate monomers, while specific examples of an ethylene glycol acrylate monomer include acrylate monomers such as polyethylene glycol monoacrylate, methoxypolyethylene glycol monoacrylate, and polyethylene glycol monoacrylate and the like.

A further aspect of the present invention is a reference electrode having the above-described reference electrode internal solution.

A further aspect of the present invention is a glass electrode that is used together with the above-described reference electrode, and that is equipped with responsive glass containing $Me_2O_3$ (wherein Me is lanthanide).

By employing this type of structure, because the responsive glass contains at least lanthanide, it becomes difficult for measurement errors to occur when measuring an alkaline test sample, and it is possible to stably and accurately measure a broad pH range of test samples.

In order to further improve the durability by strengthening the glass framework, it is preferable for the responsive glass to contain $Y_2O_3$ or $Sc_2O_3$.

More specifically, if the responsive glass contains $Y_2O_3$, then it is possible to improve the durability thereof while suppressing measurement errors that occur when measuring an alkaline test sample. Moreover, if the responsive glass contains $Sc_2O_3$, then although it does become slightly easier for the above-described measurement errors to occur, the effect is achieved that the improvement in durability is particularly conspicuous.

Furthermore, the present invention is also an electrochemical measurement device that includes the above-described glass electrode, a computation unit that outputs measurement data showing measurement results based on output values from the glass electrode and the reference electrode, and a display unit that displays the measurement results based on the measurement data output from the computation unit.

According to an electrochemical measurement device having the above-described structure, it is possible for the above-described operation and effects to be obtained.

Advantageous Effects of the Invention

According to the present invention which has the above-described structure, it is possible to improve the durability of a reference electrode internal solution beyond what is obtainable from the conventional technology.

DESCRIPTION OF THE REFERENCE NUMERALS

Figure 1:
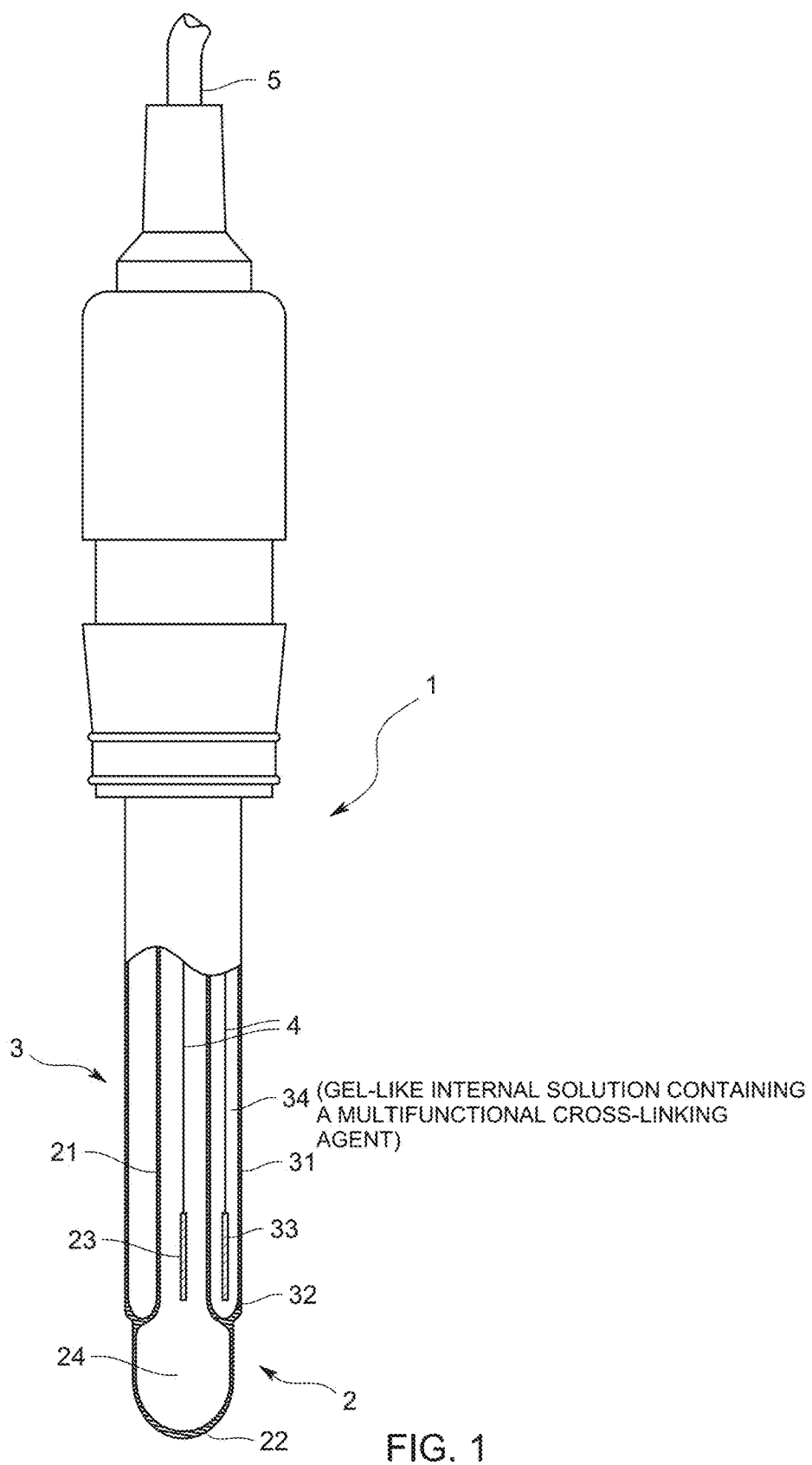
FIG. 1 is a typical view showing the structures of a glass electrode and a reference electrode of the present embodiment.

1 . . . Composite electrode
2 . . . Glass electrode
22 . . . Responsive glass
23 . . . Inner pole for glass electrode
24 . . . Internal solution for glass electrode
3 . . . Reference electrode
32 . . . Liquid junction portion
33 . . . Reference electrode inner pole
34 . . . Reference electrode internal solution

DESCRIPTION OF THE EMBODIMENTS

Hereinafter, an embodiment of the present invented will be described.

An electrochemical measurement device according to the present embodiment is equipped with a reference electrode 3, a glass electrode 2, a computing unit (not shown) such as, for example, a computer that outputs measurement data showing measurement results such as the pH and the like of a test sample based on output values from the reference electrode 3 and the glass electrode 2, and a display unit (not shown) such as a display that displays measurement results based on the measurement data output from the computing unit.

As is shown in FIG. 1, the reference electrode 3 is provided so as to surround the circumference of the glass electrode 2 and, by being formed integrally with the glass electrode 2, forms a composite electrode 1.

The glass electrode 2 is provided with a circular cylinder-shaped glass electrode supporting tube 21, responsive glass 22 that is provided at a distal end portion of the glass electrode supporting tube 21, and a glass electrode inner pole 23.

The glass electrode supporting tube 21 houses the glass electrode inner pole 23, and is filled with, for example, a KCl solution having a pH of 7 that serves as a glass electrode internal solution 24.

An Ag/AgCl electrode is used for the glass electrode inner pole 23, and one end side of a lead line 4 is connected thereto, while another end side of the lead line 4 is connected to a cable 5 so as to be conductively joined to, for example, a pH meter main body (not shown).

The responsive glass 22 is formed integrally with the glass electrode supporting tube 21 by being electrically joined by welding (i.e., thermal welding) or the like to a distal end portion of the glass electrode supporting tube 21.

More specifically, the responsive glass 22 of the present embodiment has a composition that contains at least $La_2O_3$, and additionally contains $Y_2O_3$ and $Sc_2O_3$ in smaller quantities than the $La_2O_3$.

The reference electrode 3 is provided with a substantially circular cylinder-shaped glass reference electrode supporting tube 31, a liquid junction portion 32 that penetrates a distal end side of the reference electrode supporting tube 31 in the thickness direction thereof, and a reference electrode inner pole 33.

More specifically, a distal end portion of this reference electrode supporting tube 31 is connected in an airtight manner by welding (i.e., thermal welding) or the like to the vicinity of a junction portion between the glass electrode supporting tube 21 and the responsive glass 22. The reference electrode supporting tube 31 is provided such that it surrounds the outer circumference of the glass electrode supporting tube 21. A portion (i.e., a space) that is enclosed between an inner side of the reference electrode supporting tube 31 and the outer side (i.e., the outer circumference) of the glass electrode supporting tube 21 houses the reference electrode inner pole 33, and is filled with a reference electrode internal solution 34 (described below).

An Ag/AgCl electrode or the like is used for the reference electrode inner pole 33 and, in the same way as in the glass electrode inner pole 23, one end side of a lead line 4 is connected thereto, while another end side of the lead line 4 is connected to a cable 5 so as to be conductively joined to the pH meter main body (not shown).

The liquid junction portion 32 is formed by sealing a porous sintered body into a hole that has been provided in advance in an outer circumferential wall of the reference electrode supporting tube 31, and then creating pinholes in this porous sintered body using a laser or the like.

Note that it is also possible to form the liquid junction portion 32 by forming a small through hole in the reference electrode supporting tube 31 so that the action of a liquid junction is demonstrated in the reference electrode internal solution 34 (described below).

If the above-described structure is employed, then by immersing the responsive glass 22 in a test sample whose pH is to be measured, an electromotive force is generated that corresponds to the pH difference between the glass electrode internal solution 24, whose pH is already known, and the test sample, and the pH of the test sample can be measured by detecting this electromotive force using the glass electrode 2 and the reference electrode 3.

The reference electrode internal solution 34 of the present embodiment is a gel-like substance that is manufactured by copolymerizing a monofunctional hydrophilic monomer and a cross-linking agent having a plurality of functional groups (multifunctional groups). However, acrylamide and methacrylamide are excluded from being used for either the aforementioned cross-linking agent having a plurality of functional groups or the hydrophilic monomer.

Examples of a cross-linking agent include substances that contain a plurality of polymerizable double bonds, and substances that have a plurality of functional groups having intramolecular reactivity.

More specifically, the cross-linking agent is a monomer having a plurality of functional groups, and examples thereof include acrylates having a plurality of functional groups, methacrylates having a plurality of functional groups, amines having a plurality of functional groups, and vinyl compounds having a plurality of functional groups, and the like. Examples of an acrylate or methacrylate include glycerine diacrylate, polyalkylene glycol diacrylate, polyalkylene glycol triacrylate, ethoxylated bisphenol A diacrylate, ethoxylated glycerine triacrylate, trimethylolpropane triacrylate, trimethylolpropane trimethacrylate, polyalkylene glycol dimethacrylate, glycerine dimethacrylate, polyalkylene glycol trimethacrylate, and the like. Examples of an amine having a plurality of functional groups include triethylenetetramine, ethylenediamine, hexamethylenediamine, dipropylenetriamine, and the like. Examples of a vinyl compound having a plurality of functional groups include divinylbenzene, butanediol divinyl ether, diethylene glycol divinyl ether, and the like.

Examples of a hydrophilic monomer include alkylaminoalkyl acrylates, and polyhydric alcohol acrylates, as well as alkoxy ether derivatives thereof, acryloyloxy ethyl succinic acid, acryloyloxy ethyl acid phosphates, 2-(acryloyloxy) ethane sulfonic acid, 3-sulfopropyl potassium acrylates, alkyl amino alkyl methacrylates, and polyhydric alcohol methacrylates, as well as alkoxy ether derivatives thereof, methacryloyloxy ethyl succinic acid, methacryloyloxy ethyl acid phosphates, 2-(methacryloyloxy) ethane sulfonic acid, 3-sulfopropyl potassium methacrylates, and the like.

Examples of the aforementioned alkyl amino alkyl methacrylates include dimethylaminoethyl methacrylates as well as quaternary compounds thereof, diethylaminoethyl methacrylates as well as quaternary compounds thereof, dipropylaminoethyl methacrylates as well as quaternary compounds thereof, N, N, N-trimethyl-(2-hydroxy-3-methacryloyloxy) propyl ammonium chloride, and the like.

Examples of the aforementioned alkyl amino alkyl acrylates include dimethylaminoethyl acrylates as well as quaternary compounds thereof, diethylaminoethyl acrylates as well as quaternary compounds thereof, dipropylaminoethyl acrylates as well as quaternary compounds thereof, N, N, N-trimethyl-(2-hydroxy-3-acryloyloxy) propyl ammonium chloride, and the like.

Examples of a polyhydric alcohol methacrylate and alkoxy ether derivatives thereof include glycerine methacrylate, and ethylene glycol methacrylate monomers, while specific examples of an ethylene glycol methacrylate monomer include methacrylate monomers such as polyethylene glycol monomethacrylate, methoxypolyethylene glycol monomethacrylate, and polyethylene glycol monomethacrylate and the like.

Examples of a polyhydric alcohol acrylate and alkoxy ether derivatives thereof include glycerine acrylate, and ethylene glycol acrylate monomers, while specific examples of an ethylene glycol acrylate monomer include acrylate monomers such as polyethylene glycol monoacrylate, methoxypolyethylene glycol monoacrylate, and polyethylene glycol monoacrylate and the like.

According to the reference electrode 3 that uses the reference electrode internal solution 34 that is formed in this manner, superior pressure resistance and heat resistance are achieved compared to the conventional technology, and it is possible, for example, to reduce deterioration that is caused by repeated steam sterilization.

Moreover, the reference electrode internal solution 34 of the present embodiment also makes it possible to improve measurement accuracy by reducing the liquid junction potential that is generated in an alkaline test sample to a greater extent than is obtainable from the conventional technology.

Furthermore, by copolymerizing the above-described substances, although the reference electrode internal solution used in the present invention is in a gel-like form, for example, by using a monomer having a plurality of functional groups as a cross-linking agent, and copolymerizing this cross-linking agent together with a monofunctional monomer, a cross-linking structure can be created inside the molecules, and this structure makes it possible to prevent elution and swelling of the material even when processing is repeatedly performed at high temperatures,. As a result, this reference electrode internal solution 34 has superior durability against repeated high-temperature processing such as steam sterilization.

Furthermore, when, for example, copolymerization is performed using only a monomer having a plurality of functional groups, there is a tendency for the obtained gel to become too hard, and the gel has poor stability in resistance to temperature changes. Moreover, if only a monofunctional monomer is used, then there is a tendency for the stability of the liquid junction potential, the repetition durability, and the stability in resistance to temperature changes to be inadequate. Furthermore, if the monofunctional monomer is hydrophobic, then it is not possible for a KCl solution to be used and the stability of the gel deteriorates. Accordingly, a hydrophilic monomer is used.

As has been described above, by using a monofunctional hydrophilic monomer in combination with a cross-linking agent, the effects of improved stability of the liquid junction potential, improved repetition durability, and improved stability in resistance to temperature changes are achieved, and the performance of the electrode is thereby improved.

Furthermore, because the responsive glass contains at least $La_2O_3$, it is difficult for errors to appear on the alkaline side. Moreover, because small quantities of $Y_2O_3$ and $Sc_2O_3$ are additionally contained, the durability is further improved by the strengthened glass framework.

More specifically, if the responsive glass 22 contains $Y_2O_3$, then it is possible to improve the durability thereof while suppressing errors that occur when measuring an alkaline test sample. If the responsive glass 22 contains $Sc_2O_3$, then although it does become slightly easier for the above-described measurement errors to occur, the effect is achieved that the improvement in durability is particularly conspicuous.

As a result, by including favorable quantities of these constituents, as is described above, it is possible to improve the durability while suppressing measurement errors on the alkaline side.

Furthermore, by including Sc, the responsive glass 22 is furnished with excellent heat resistance.

Note that the present invention is not limited to the above-described embodiment.

For example, in the above-described embodiment the glass electrode 2 and the reference electrode 3 are formed as a single integral object, however, it is also possible to employ a structure in which these electrodes are mutually independent objects.

In addition to this, the present invention is not limited to the above-described embodiment and various modifications and the like may be made thereto insofar as they do not depart from the spirit or scope of the present invention.

EXAMPLES

Next, a method of manufacturing the reference electrode internal solution 34 of the present invention as well as experiment results will be described specifically.

As is shown in Table 1, the reference electrode internal solution 34 of the present embodiment is obtained by copolymerizing a hydrophilic monomer and a cross-linking agent. In Table 1, a sample x, which is a conventional reference electrode internal solution, is also shown as a comparative example. Note that this sample x is an electrode that uses a polymer gel, and does not contain a cross-linking agent.

TABLE 1

| Sample | Hydrophilic monomer A | Hydrophilic monomer B | Cross-linking agent A | Cross-linking agent B | 3.0M-KCl | Additives A | Additives B | Additives C |
|---|---|---|---|---|---|---|---|---|
| a | 10 | 0 | 10 | 0 | 80 | 1 | 1 | 1 |
| b | 10 | 0 | 0 | 10 | 80 | 1 | 1 | 1 |
| c | 2.5 | 2.5 | 0 | 5 | 90 | 1 | 1 | 1 |
| d | 2.5 | 5 | 0 | 2.5 | 90 | 1 | 1 | 1 |
| e | 5 | 5 | 0 | 5 | 85 | 1 | 1 | 1 |
| x | (Comparative example) | | | | | | | |

As is shown in Table 1, each sample in the present example is manufactured using either hydrophilic monomer A or hydrophilic monomer B, and using either cross-linking agent A or cross-linking agent B, and by copolymerizing these substances. Specifically, taking sample a as an example, a hydrophilic monomer A and a cross-linking agent A are injected together with additives into 3.0 mol/L of a KCl solution. After this has become a uniform solution, it is placed inside a glass tube that is to be used for the electrode and copolymerization is carried out by performing heat processing thereon. As a result, sample a is obtained.

Here, the hydrophilic monomers A and B are monofunctional hydrophilic monomers from which acrylamides and methacrylamides are excluded. The hydrophilic monomer A of the present embodiment is glycerine monomethacrylate, while the hydrophilic monomer B of the present embodiment is a quaternary compound of dimethylaminoethyl methacrylate.

The cross-linking agent A of the present embodiment is glycerine diacrylate, while the cross-linking agent B of the present embodiment is trimethylolpropane trimethacrylate.

Note that triethylenetetramine is used as the additive A, ammonium persulfate is used as the additive B, and 2,2'-azobis [N-(2-carboxyethyl)-2-methylpropionamidine]hydrate is used as the additive C.

The experiment results obtained when the properties of each of the samples manufactured in the above-described manner were evaluated are shown in FIG. 2 through FIG. 5, and are described below in detail.

Figure 2:
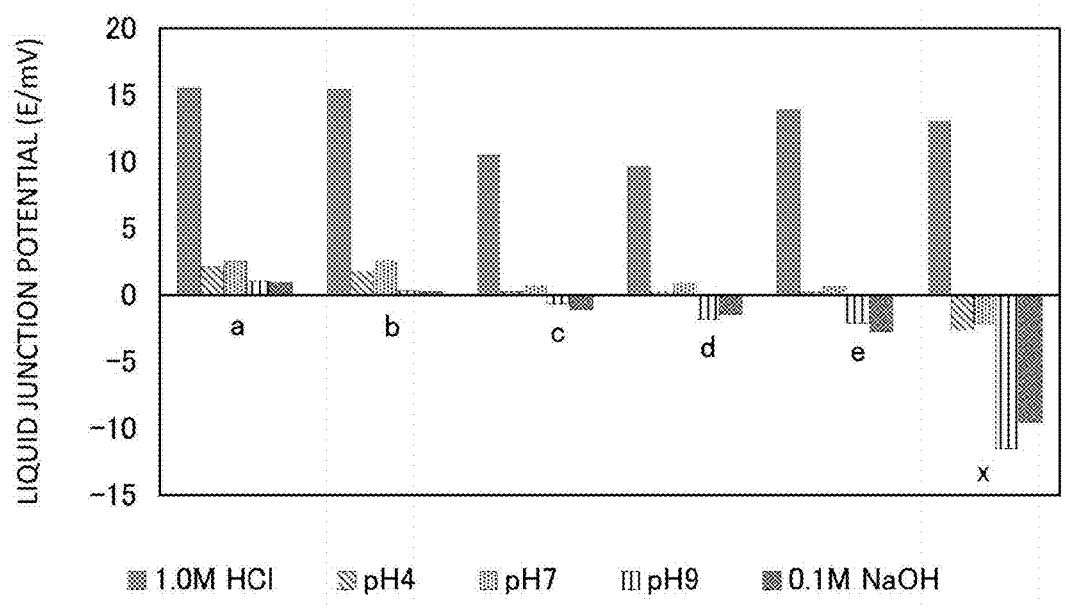
FIG. 2 is a graph showing the results of an experiment using the internal solution of a reference electrode according to the present embodiment.

In FIG. 2, the experiment results obtained when the liquid junction potentials of the reference electrode 3 when each of the samples was used as the reference electrode internal solution 34, and a reference comparison electrode that exhibited stability over a broad range of pH were measured are shown.

From this graph it can be understood that, compared to the conventional sample x, in each case when the samples a, b, c, d, and e are used, the liquid junction potential is reduced over a wide pH range. This trend is particularly conspicuous in the case of alkaline test samples.

Figure 3:
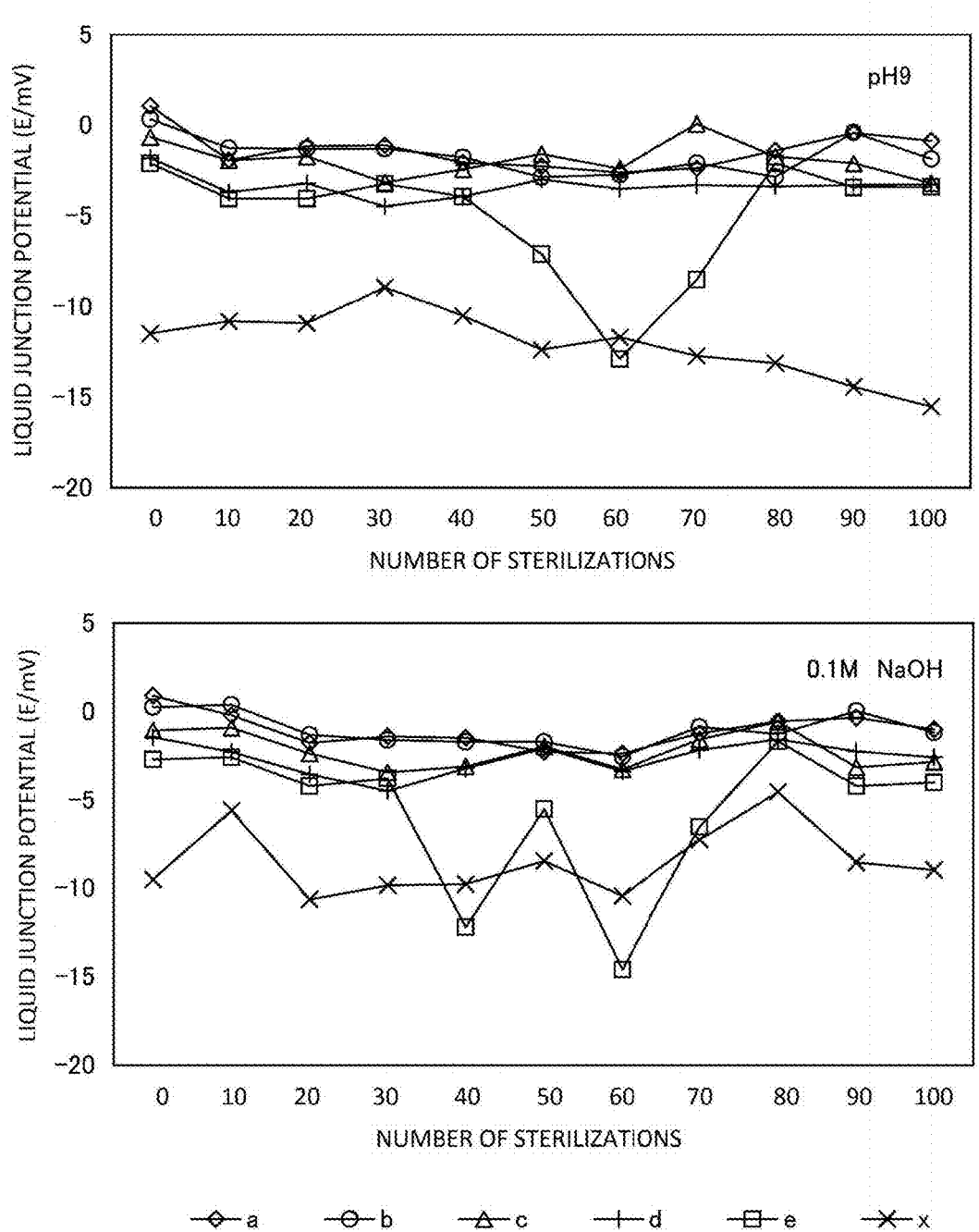
FIG. 3 is a graph showing the results of an experiment using the internal solution of a reference electrode according to the present embodiment.

In FIG. 3, the experiment results obtained when the liquid junction potentials of the reference electrode 3 when each of the samples was used as the reference electrode internal solution 34, and a reference comparison electrode that exhibited stability over a broad range of pH were measured after steam sterilization was repeated a number of times are shown. Note that the upper portion of FIG. 3 shows experiment conditions in which the test sample has a pH of 9, while the lower portion of FIG. 3 shows experiment conditions in which the test sample is 0.1 MNaOH.

From this graph it can be understood that, compared to the conventional sample x, in each case when the samples a, b, c, d, and e were used, the liquid junction potential was stable over a wide pH range irrespective of the number of times steam sterilization was repeated. Improved pressure resistance and heat resistance can also be seen.

Figure 4:
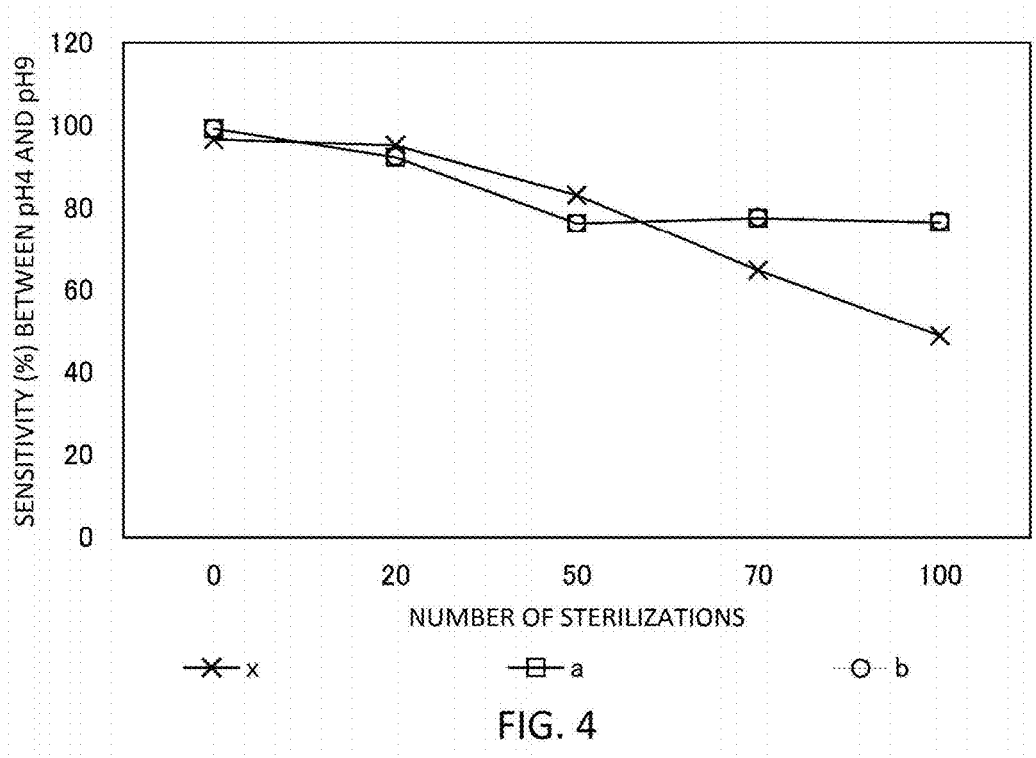
FIG. 4 is a graph showing the results of an experiment using the internal solution of a reference electrode according to the present embodiment.

In FIG. 4, the experiment results obtained when the sensitivity deterioration is observed when the reference electrode 3 in which each of the samples is used as the reference electrode internal solution 34, and a glass electrode containing KCl as its internal solution are repeatedly inserted in a sterilization autoclave (at 130° C.) are shown. Note that the electrode shown in Table 2 is used as the glass electrode.

TABLE 2

| Composition (mol %) | | | | | | | |
|---|---|---|---|---|---|---|---|
| $SiO_2$ | $Li_2O_3$ | $Sc_2O_3$ | $La_2O_3$ | $Cs_2O_3$ | BaO | $Ta_2O_3$ | Total |
| 64.5 | 26 | 0.5 | 3 | 2 | 2 | 2 | 100 |

From the graph shown in FIG. 4 it can be understood that when samples a and b are used, compared with the conventional sample x, there is no reduction in the measurement sensitivity even when the number of sterilizations is increased. Namely, when samples a and b are used, it can be said that not only is the durability maintained when these are used in combination with a glass electrode, but the steam sterilization has only a minimal effect on the measurement sensitivity.

Figure 5:
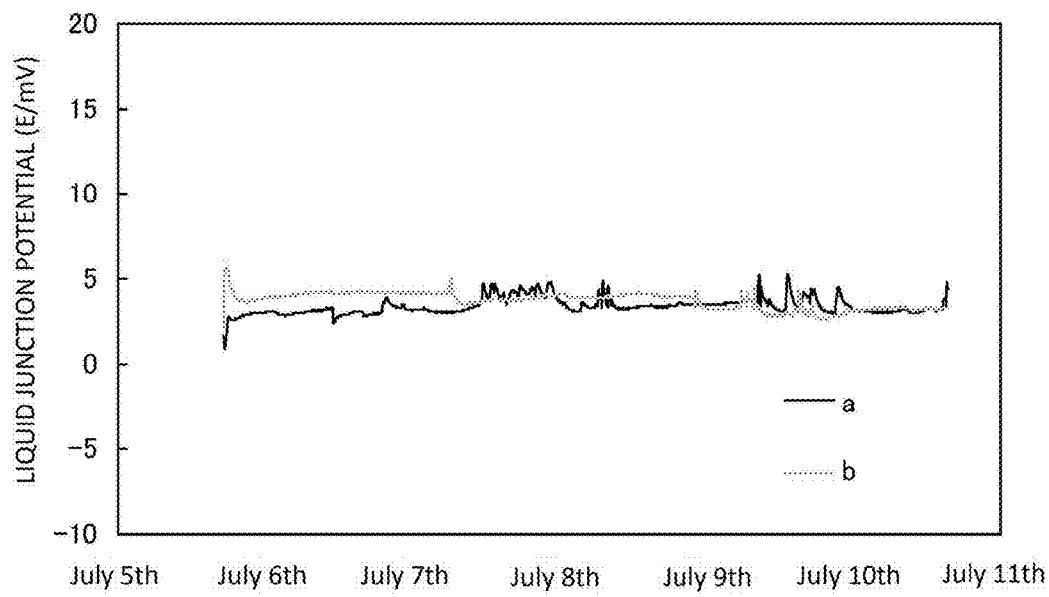
FIG. 5 is a graph showing the results of an experiment using the internal solution of a reference electrode according to the present embodiment.

In FIG. 5, the experiment results obtained when the samples are immersed in a thermostatic bath at 25" in a standard liquid having a pH of 7, and variations in the liquid junction potential are observed are shown.

From this graph it can be understood that, in the samples a and b of the present example, any occurrence of a liquid junction potential is suppressed even after a considerable number of days has elapsed, so that by using these samples for the reference electrode internal solution 34, stable measurements are able to be made.

In addition to the above-described experiment results, the results obtained when each of the samples is used as the reference electrode internal solution 34, and the color of each sample is compared (i.e., to evaluate its appearance as a product) after that particular reference electrode 3 is steam sterilized are shown in Table 3.

Note that the color of the sample referred to here is actually a transparent color before the steam sterilization, and if this color changes because of the steam sterilization, then this change in appearance makes the sample unsuitable for use as a product.

TABLE 3

| | | Stability | | | | |
|---|---|---|---|---|---|---|
| Sample | Liquid junction potential | Temperature stability: 0~70° C. | | Long-term stability | | Overall |
| | | Acidic pH 2 | Alkaline pH 12 | Standard liquid 7 | Color | |
| a | ○ | ○ | ○ | ○ | Transparent | ○ |
| b | ○ | Δ | Δ | ○ | Transparent | ○ |
| c | ○ | Δ | ○ | ○ | Peach | Δ |
| d | ○ | ○ | ○ | ○ | White | ○ |
| e | ○ | ○ | ○ | ○ | Semi-transparent | ○ |
| x | X | Δ | ○ | — | White | X |

Here, the references used to determine the stability described in the above tables were taken as: ○=a liquid junction potential of within ±6 mV; Δ=a liquid junction potential of within ±12 mV; and X=a liquid junction potential of more than ±12 mV.

From the experiment results shown in FIG. 2 through FIG. 5, and from the overall determination given in Table 3 it can be understood that samples a, b, d, and e are favorable to be used as the reference electrode internal solution 34.

Note that the present invention is not limited to the above described examples.

INDUSTRIAL APPLICABILITY

According to the present invention, it is possible to improve the durability of a reference electrode internal solution beyond what is obtainable from the conventional technology.

The invention claimed is:

1. An electrochemical measurement device comprising:

a glass electrode that is equipped with responsive glass; and a comparison electrode having a reference electrode internal solution containing a copolymerization of a cross-linking agent having a plurality of functional groups excluding acrylamide, and a monofunctional hydrophilic monomer excluding acrylamide, wherein the responsive glass contains $Me_2O_3$, wherein Me is a lanthanide;

the cross-linking agent is at least one substance selected from the group consisting of acrylates having a plurality of functional groups, methacrylates having a plurality of functional groups, amines having a plurality of functional groups and vinyl compounds having a plurality of functional groups; and the monofunctional hydrophilic monomer is at least one substance selected from the group consisting of polyhydric alcohol acrylates, as well as alkoxy ether derivatives thereof, acryloyloxy ethyl succinic acid, acryloyloxy ethyl acid phosphates, 2-(acryloyloxy) ethane sulfonic acid, 3-sulfopropyl potassium acrylates, and polyhydric alcohol methacrylates, as well as alkoxy ether derivatives thereof, methacryloyloxy ethyl succinic acid, methacryloyloxy ethyl acid phosphates, 2-(methacryloyloxy) ethane sulfonic acid, and 3-sulfopropyl potassium methacrylates.

2. The electrochemical measurement device according to claim 1, wherein the responsive glass contains $Y_2O_3$ or $Sc_2O_3$.

3. The electrochemical measurement device according to claim 1, further comprising:

a computation unit that outputs measurement data showing measurement results based on output values from the glass electrode and the reference electrode; and a display unit that displays the measurement results based on the measurement data output from the computation unit.

* * * * *